United States Patent
Ching et al.

(10) Patent No.: US 10,987,448 B2
(45) Date of Patent: *Apr. 27, 2021

(54) OSTEOCONDUCTIVE AND OSTEOINDUCTIVE IMPLANT FOR AUGMENTATION, STABILIZATION, OR DEFECT RECONSTRUCTION

(71) Applicant: UNIVERSITY OF SOUTH FLORIDA, Tampa, FL (US)

(72) Inventors: Jessica A. Ching, Toronto (CA); Jonathan Michael Ford, Tampa, FL (US); Summer Joy Decker, Apollo Beach, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/843,946

(22) Filed: Dec. 15, 2017

(65) Prior Publication Data

US 2018/0126034 A1 May 10, 2018

Related U.S. Application Data

(63) Continuation of application No. PCT/US2015/038599, filed on Jun. 30, 2015.

(51) Int. Cl.
| | |
|---|---|
| A61L 27/26 | (2006.01) |
| A61L 27/36 | (2006.01) |
| A61L 27/54 | (2006.01) |
| A61F 2/28 | (2006.01) |
| A61L 27/46 | (2006.01) |
| A61L 27/18 | (2006.01) |
| A61L 27/56 | (2006.01) |

(52) U.S. Cl.
CPC ............ A61L 27/26 (2013.01); A61F 2/2846 (2013.01); A61L 27/18 (2013.01); A61L 27/3608 (2013.01); A61L 27/3645 (2013.01); A61L 27/46 (2013.01); A61L 27/54 (2013.01); A61L 27/56 (2013.01); A61L 2300/414 (2013.01); A61L 2430/02 (2013.01); A61L 2430/12 (2013.01); A61L 2430/38 (2013.01)

(58) Field of Classification Search
CPC ............... A61L 2430/02; A61L 27/54; A61L 2300/112412; A61L 27/3608; A61L 27/26; A61L 2300/112; A61L 2300/412; A61F 2002/2835; A61F 2002/4495; A61F 2002/30062
See application file for complete search history.

(56) References Cited

U.S. PATENT DOCUMENTS

| | | |
|---|---|---|
| 5,948,020 A | 9/1999 | Yoon et al. |
| 8,945,536 B2 | 2/2015 | Lui et al. |
| 2002/0090725 A1* | 7/2002 | Simpson ................. A61L 15/32 435/402 |
| 2004/0038348 A1 | 2/2004 | Pena et al. |
| 2004/0230309 A1 | 11/2004 | DiMauro et al. |
| 2005/0010304 A1 | 1/2005 | Jamali |
| 2005/0107795 A1 | 5/2005 | Morris et al. |
| 2007/0160681 A1* | 7/2007 | Park ....................... A61K 38/10 424/548 |
| 2007/0254042 A1* | 11/2007 | Drapeau ................. A61L 27/20 424/550 |
| 2007/0255422 A1 | 11/2007 | Wei et al. |
| 2008/0044449 A1 | 2/2008 | McKay |
| 2010/0049330 A1 | 2/2010 | Horvath |
| 2010/0172951 A1 | 7/2010 | Wasielewski |
| 2011/0087314 A1* | 4/2011 | Diederich ............... A61N 7/022 607/113 |
| 2012/0029102 A1 | 2/2012 | Rose et al. |
| 2013/0189338 A1* | 7/2013 | Drapeau ................. A61K 38/20 424/402 |
| 2014/0277569 A1 | 9/2014 | Lange |
| 2015/0010607 A1 | 1/2015 | Francis et al. |
| 2015/0050358 A1 | 2/2015 | Seong et al. |
| 2016/0038641 A1* | 2/2016 | Cashman ............... A61K 35/28 424/423 |

FOREIGN PATENT DOCUMENTS

| | | | |
|---|---|---|---|
| JP | 2009-541358 A | 11/2009 | |
| JP | 2010-500905 A | 1/2010 | |
| JP | 2010-505480 A | 2/2010 | |
| JP | 2011-528960 A | 12/2011 | |
| JP | 2014-111130 A | 6/2014 | |
| WO | WO-2008/021921 A2 | 2/2008 | |
| WO | WO-2013119873 A1 * | 8/2013 | ............. A61K 35/28 |

OTHER PUBLICATIONS

Brandt et al. (Journal of Material Science: Materials in Medicine, vol. 21,2010, pp. 283-294) (Year: 2010).*

(Continued)

*Primary Examiner* — Mark V Stevens

(74) *Attorney, Agent, or Firm* — Quarles & Brady LLP

(57) ABSTRACT

Aspects of the present invention provide implants for augmentation, stabilization, or defect reconstruction of bone tissue, comprising a scaffold portion structured to provide shape to the implant, the scaffold portion comprising one or more of the following: one or more polylactic acid isomer; one or more polyglycolic acid isomer; and/or allogenic bone material, or similar compound.

6 Claims, 4 Drawing Sheets

(56) References Cited

OTHER PUBLICATIONS

Sykaras et al (Journal of Oral Science, vol. 45, 2003, pp. 57-73) (Year: 2003).*
International Search Report in International Application No. PCT/US2015/038599, filed Jun. 30, 2015.
Office Action dated Dec. 21, 2018 in Japanese Application No. 2017-568286, along with its English Translation.
Supplemental European Search Report dated Feb. 28, 2019 in European Application No. 15897341.2.
Glowacki, J. et al., "Application of the Biological Principle of Induced Osteogenesis for Craniofacial Defects," *The Lancet*, May 2, 1981, 1(8227):959-962, The Lancet Ltd.
Mulliken, J. B. et al., "Induced Osteogenesis—The Biological Principle and Clinical Applications," *Journal of Surgical Research*, 1984, 37:487-496, Academic Press, Inc.
Rosenthal, R. K. et al., "Demineralized Bone Implants for Nonunion Fractures, Bone Cysts, and Fibrous Lesions," *Clinical Orthopaedics and Related Research*, Jul. 1999, 364:61-69, Lippincott Williams & Wilkins, Inc.
Sassard, W. R. et al., "Augmenting Local Bone With Grafton Demineralized Bone Matrix for Posterolateral Lumbar Spine Fusion: Avoiding Second Site Autologous Bone Harvest," *Orthopedics*, Oct. 2000, 23(10):1059-1065.
Tiedeman, J. J. et al., "The Role of a Composite, Demineralized Bone Matrix and Bone Marrow in the Treatment of Osseous Defects," *Orthopedics*, Dec. 1995, 18(12):1153-1158,.
Urist, M. R. et al., "Bone Cell Differentiation and Growth Factors," *Science*, May 13, 1983, 220(4598):680-686, American Association for the Advancement of Science.
Urist, M. R. et al., "Bone Formation in Implants of Partially and Wholly Demineralized Bone Matrix Including Observations on Acetone-fixed Intra and Extracellular Proteins," *Clinical Orthopaedics and Related Research*, Jul.-Aug. 1970, 71:271-278.
Urist, M. R. et al., "Inductive Substratum for Osteogenesis in Pellets of Particulate Bone Matrix," *Clinical Orthopaedics and Related Research*, Nov.-Dec. 1968, 61:61-78.
Examination Report dated Oct. 22, 2019 in Australian Application No. 2015401221.

* cited by examiner

OSTEOCONDUCTIVE AND OSTEOINDUCTIVE IMPLANT FOR AUGMENTATION, STABILIZATION, OR DEFECT RECONSTRUCTION

CROSS-REFERENCE TO RELATED APPLICATION

This application is a continuation of International Patent Application No. PCT/US2015/038599, filed Jun. 30, 2015, the disclosure of which is incorporated herein by reference in its entirety.

BACKGROUND OF THE INVENTION

Bone allografts, polylactic acid isomers, and polyglycolic acid isomers have established independent efficacy in the treatment of bone defects and bone reconstruction in multiple clinical situations; however, there are currently no structural implants that offer osteoconductive and osteoinductive capabilities.

BRIEF SUMMARY OF THE INVENTION

Aspects of the present invention combine allogenic bone material, such as, e.g., demineralized bone matrix or bone allograft: polylactic acid (PLA) isomers; and polyglycolic acid (PGA) isomers, or similar compounds, such as, for example, a mixture of PLA and PGA polymers (PLEA polymer) or polydioxanone (PDS) into a single implant both in plate configurations and in three-dimensional (3D) configurations, whether as a predetermined standard arrangement or customized form. Implants of the present invention address skeletal reconstruction through replacing, augmenting, or buttressing the patient's native bone.

In one aspect, the present invention provides implants for augmentation, stabilization, or defect reconstruction of bone tissue, comprising a scaffold portion structured to provide shape to the implant, the scaffold portion comprising one or more of the following: one or more polylactic acid isomer (or similar compound); one or more polyglycolic acid isomer (or similar compound); and allogenic bone material (or similar compound).

In some embodiments, the allogenic bone material comprises demineralized bone matrix.

In some embodiments, the scaffold portion is in the form of a mesh or lattice structure, or a combination of both.

In some embodiments, the implant further comprises an autologous bone graft embedded within the scaffold portion. In other embodiments, the implant further comprises bone morphogenic protein embedded within the scaffold portion.

In another aspect, the present invention provides methods for augmentation, stabilization, or defect reconstruction of bone tissue, comprising applying an implant as described herein to a site in need of augmentation, stabilization, or defect reconstruction of bone tissue.

The implants and processes herein described can be used in connection with pharmaceutical, medical, and veterinary applications, as well as fundamental scientific research and methodologies, as would be identifiable by a skilled person upon reading of the present disclosure. These and other objects, features, and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures.

DETAILED DESCRIPTION OF THE INVENTION

Figure 1:
FIG. 1 shows an implant of the present invention providing stabilization of a long bone.

Aspects of the present invention are directed to implants and related methods of utilizing such implants for the treatment of bone defects or for bone reconstruction.

Several aspects of the invention are described below, with reference to examples for illustrative purposes only. It should be understood that numerous specific details, relationships, and methods are set forth to provide a fuller understanding of the invention. One having ordinary skill in the relevant art, however, will readily recognize that the invention can be practiced without one or more of the specific details or practiced with other methods, protocols, reagents, cell lines, and animals. The present invention is not limited by the illustrated ordering of acts or events, as some acts may occur in different orders and/or concurrently with other acts or events. Furthermore, not all illustrated acts, steps, or events are required to implement a methodology in accordance with the present invention. Some of the techniques and procedures described or referenced herein are well understood and commonly employed using conventional methodology by those skilled in the art.

Unless otherwise defined, all terms of art, notations, and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a," "an," and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." As used herein, the terms "including," "includes," "having," "has," "with," or variants thereof, are intended to be inclusive similar to the term "comprising."

As would be understood by those of skill in the art, the implants and methods of the various aspects of the present invention are applicable to augmentation, stabilization, or defect reconstruction of bone tissue.

In one aspect, the present invention provides implants for augmentation, stabilization, or defect reconstruction of bone tissue, comprising a scaffold portion structured to provide shape to the implant, the scaffold portion comprising one or more of the following: one or more polylactic acid (PLA) isomer, or similar compound; one or more polyglycolic acid (PGA) isomer, or similar compound; and/or allogenic bone material, or similar compound. The compounds may be combined in varying ratios depending on the desires or needs of the clinical situation, allowing for a significant amount of customization. The mixture ratios and mesh densities are variable based on what part of the body is being repaired or augmented. The location and any potential forces that might act upon the implant are taken into consideration by the clinician. For example, a looser mesh geometry is workable in a chin or cheek implant; long bones or load bearing bones require a denser mesh for more support. These ratios may be determined by the clinician on a case by case basis depending on the treatment goals and needs of the patient and scenario, and the ratios are readily determinable by one skilled in the art. As such, the scaffold portion can comprise a single compound or multiple compounds depending on the benefits and drawbacks of each compound when used in a particular ratio and/or position in the body, which is a matter of design choice by the clinician on a case by case basis.

In some embodiments, one or more polylactic acid (PLA) isomer, or similar compound, comprises about 10%; about 20%; about 30%; about 40%; about 50%; about 60%; about 70%; about 80%; about 90%; about 100%; 0% to about 100%; about 1% to about 100%; about 10% to about 100%; about 20% to about 100%; about 30% to about 100%; about 40% to about 100%; about 50% to about 100%; about 60% to about 100%; about 70% to about 100%; about 80% to about 100%; about 90% to about 100%; 0% to about 90%; about 10% to about 80%; about 20% to about 70%; about 30% to about 60%; about 40% to about 50%; 0% to about 80%; 0% to about 70%; 0% to about 60%; 0% to about 50%; 0% to about 40%; 0% to about 30%; 0% to about 20%; 0% to about 10%; or 0% of the implant.

In some embodiments, the one or more polyglycolic acid (PGA) isomer, or similar compound, comprises about 10%; about 20%; about 30%; about 40%; about 50%; about 60%; about 70%; about 80%; about 90%; about 100%; 0% to about 100%; about 1% to about 100%; about 10% to about 100%; about 20% to about 100%; about 30% to about 100%; about 40% to about 100%; about 50% to about 100%; about 60% to about 100%; about 70% to about 100%; about 80% to about 100%; about 90% to about 100%; 0% to about 90%; about 10% to about 80%; about 20% to about 70%; about 30% to about 60%; about 40% to about 50%; 0% to about 80%; 0% to about 70%; 0% to about 60%; 0% to about 50%; 0% to about 40%; 0% to about 30%; 0% to about 20%; 0% to about 10%; or 0% of the implant.

In some embodiments, the allogenic bone material, or similar compound, comprises about 10%; about 20%; about 30%; about 40%; about 50%; about 60%; about 70%; about 80%; about 90%; about 100%; 0% to about 100%; about 1% to about 100%; about 10% to about 100%; about 20% to about 100%; about 30% to about 100%; about 40% to about 100%; about 50% to about 100%; about 60% to about 100%; about 70% to about 100%; about 80% to about 100%; about 90% to about 100%; 0% to about 90%; about 10% to about 80%; about 20% to about 70%; about 30% to about 60%; about 40% to about 50%; 0% to about 80%; 0% to about 70%; 0% to about 60%; 0% to about 50%; 0% to about 40%; 0% to about 30%; 0% to about 20%; 0% to about 10%; or 0% of the implant.

In some embodiments, the allogenic bone material comprises demineralized bone matrix (DBM). Alternative compounds that can be used in place of, or in combination with, DBM include hydroxyapatite, calcium sulfate, beta tricalcium phosphate, recombinant human bone morphogenetic proteins, bioactive glass, and combinations thereof.

PLA and PGA isomers offer in situ malleability with warming, provide strength, and are resorbable. The addition of DBM or similar compounds into the structure of the implant provides osteoinductivity and osteoconductivity, with ultimate incorporation into the final healed osseous structure; in turn, this allows the implant to facilitate osseous in-growth and increases control of the final healed osseous shape.

In some embodiments, screws, or other similar connective structures or connective compounds, can be utilized to secure the implant in place. The screws for securing the implant can be made of a similar composition as the implant or be made of any material known in the art that is useful in implants, particularly implants of bone structures.

In some embodiments, the scaffold portion is in the form of a mesh or lattice structure, or a combination of both. The mesh or lattice structure maintains its form and can be used to stabilize surrounding bony structures. The scaffold portion can be formed into a customizable, stable form; the shape and structure can also be customized as well to improve its function and overall outcome. The density of the mesh or lattice structure can be customized as well, making a tighter or looser network as determined to be desirable by the clinician.

In some embodiments, the implant further comprises an autologous bone graft embedded within the scaffold portion. In other embodiments, the implant further comprises bone morphogenic protein (BMP) embedded within the scaffold portion.

The implants of the present invention can be in the form of sheet (plate) of the scaffold structure. A three-dimensional (3D) form may also be adapted to a particular defect or to achieve the desired osseous structural change. A scaffold structure (e.g., lattice-work type structure or similar structure) affords the capability to fill the form with an autologous bone graft or BMP or an additional substrate, should this be desired. The scaffold portion or similar structure may be increased or decreased in thickness in order to decrease or increase porosity of the form, respectively. For customization of the implant, modeling may be employed based on a computerized tomography (CT) scan of the patient.

The implants of the present invention can also be 3D printed if a manufacturer possesses these capabilities. Alternatively, a mold may be fashioned from a compatible substrate and used to fashion the implants.

In another aspect, the present invention provides methods for augmentation, stabilization, or defect reconstruction of bone tissue, comprising applying an implant described herein to a site in need of augmentation, stabilization, or defect reconstruction of bone tissue. In some embodiments, the methods further comprise embedding an autologous bone graft within the scaffold portion. In other embodiments, the methods further comprise embedding BMP within the scaffold portion.

During methods of use the implant can be intraoperatively modified, as the PLA and PGA isomers become malleable when warmed. This allows for further customization. Also, since all components of the implant will be resorbed or incorporated, there is no need for hardware removal in the future.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification. All publications and patent documents cited in this application are incorporated by reference in pertinent part for all purposes to the same extent as if each individual publication or patent document were so individually denoted.

EXAMPLES

The methods and implants herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

Example 1: Implant for Stabilization of a Long Bone (Femur)

FIG. 1 shows an implant of the present invention providing stabilization of a long bone.

Example 2: Implant for Augmentation of a Chin

Figure 2:
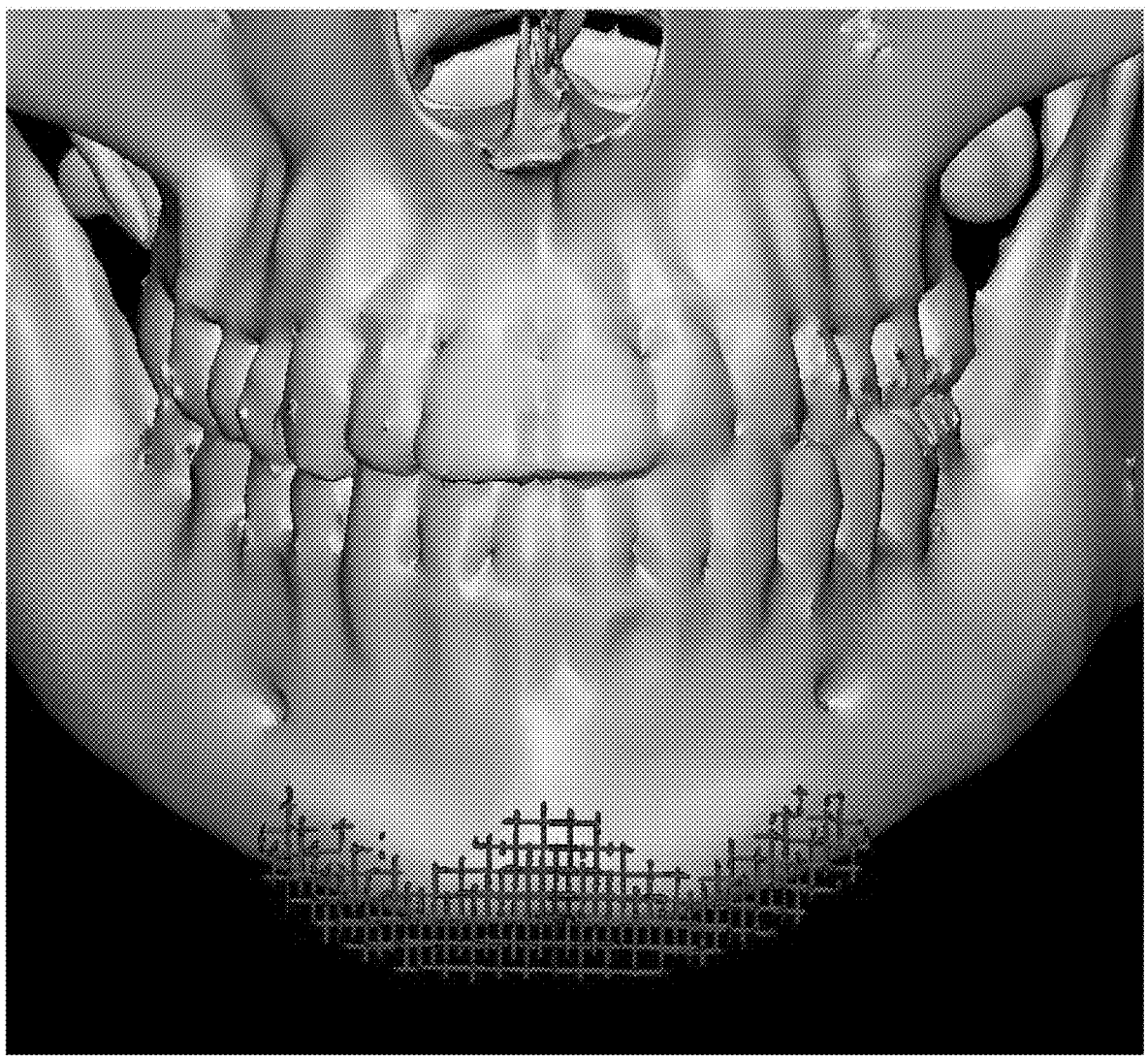
FIG. 2 shows an implant of the present invention being utilized to provide chin augmentation.

FIG. 2 shows an implant of the present invention providing chin augmentation.

Example 3: Implant for Zygoma Reconstruction

Figure 3:
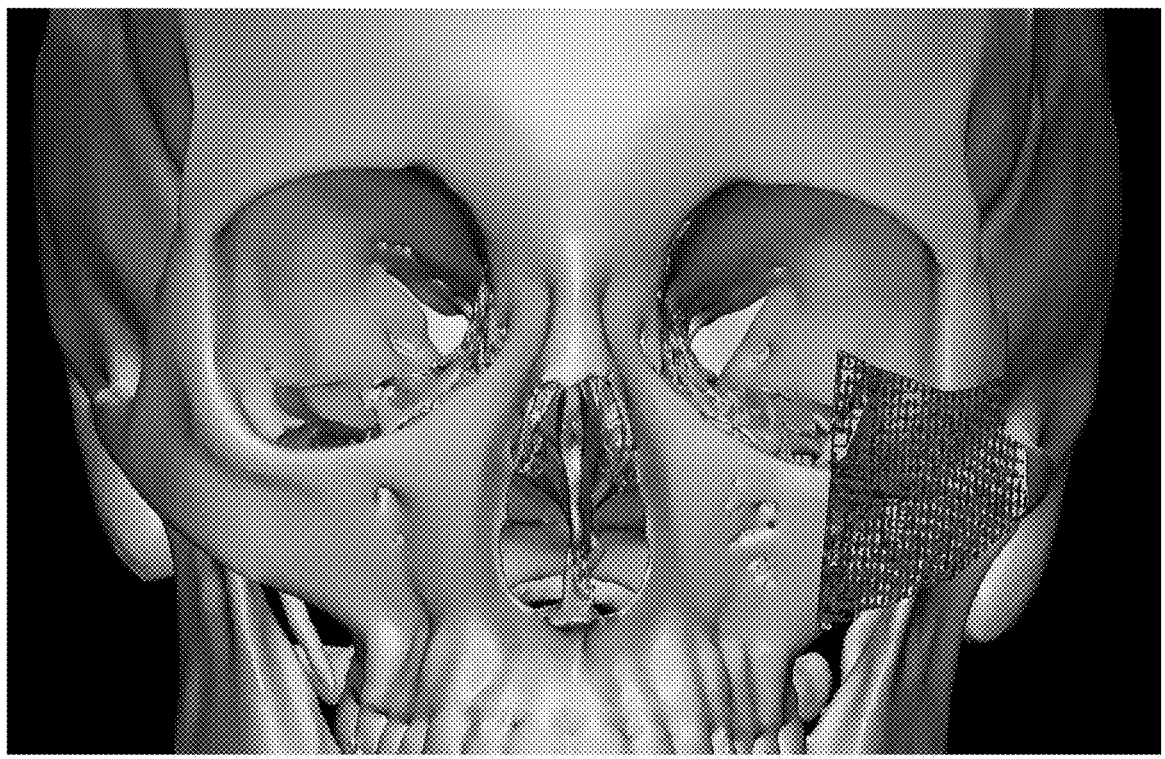
FIG. 3 shows an implant of the present invention placed in position for zygoma reconstruction viewed from the face of the skull.
Figure 4:
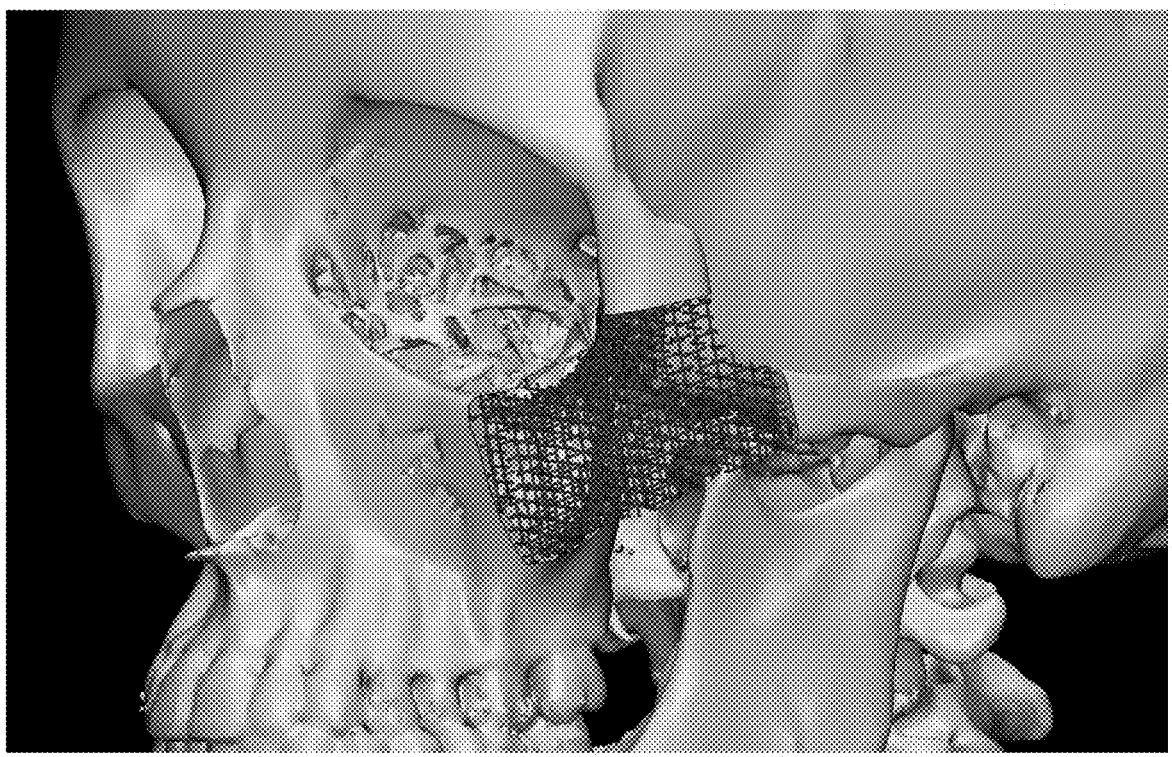
FIG. 4 shows the implant shown in FIG. 3 viewed from the side of the skull.

FIG. 3 shows an implant of the present invention placed in position for zygoma reconstruction viewed from the face of the skull. FIG. 4 shows the implant shown in FIG. 3 viewed from the side of the skull.

Example 4: Methods of Using the Implants of the Present Invention

Once the implant has been designed and manufactured, the patient is taken to the operating room and the anatomic area where the implant is to be used is exposed in the standard fashion for augmentation, stabilization, or defect reconstruction.

In the case of bone augmentation, the implant may be fitted against the surface of the bone area to be augmented, by molding or trimming the implant or by other suitable technique as known in the art. The implant can be secured with screws of a similar composition, depending on the clinical demands of the situation.

In the case of bone stabilization, including but not limited to fracture fixation or buttressing, the implant may be fitted against the surface of the bones once reduction and/or alignment has been achieved. The implant can be secured with screws of a similar composition, depending on the clinical demands of the situation.

In the case of defect reconstruction, a bone defect exists that requires intervening bone placement. In some cases, a 3D form of the implant with a type of lattice structure is utilized. This structure can be filled with autologous cancellous bone graft and/or bone morphogenic protein. The implant can be placed in contact with muscle or fascia to increase the osteoinductive and osteoconductive potential of the implant. The implant can be secured with screws of a similar composition in the standard fashion.

In all cases of use, the implant can be intraoperatively modified as the PLA and PGA isomers become malleable when warmed. This allows for further customization.

As all components of the implant are preferably resorbed or incorporated, there is inherently no need for hardware removal in the future.

DISCUSSION

The present invention provides an implant that can be used to buttress, augment, or replace the native bony skeleton. The implant is made from a combination of resorbable malleable material, osteoinductive material, and osteoconductive material, in varying proportions, depending on the specific objectives of its utilization. Not only can the proportion of materials be customized, but the shape and structure can be customized as well to improve its function and overall outcome. The customization of these implants allows for a wide range of applicability to surgical practice, and the use of the resorbable, malleable material allows for further intraoperative adjustment. While all the materials used to form the implants are independently valued, combining them into a single implant increases structural strength and allows incorporation of an implant as part of the osseous structure with time. The implants also provide a patient with a reconstructive alternative for bone replacement with or without autologous bone grafting. As all component materials of the implant are either resorbed or incorporated, there is no need for removal later as with other types of implants.

It is to be appreciated that the foregoing Detailed Description section, and not the Abstract section, is intended to be used to interpret the claims. The Abstract section may set forth one or more, but not all, exemplary embodiments of the present invention as contemplated by the inventor(s), and thus, is not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations, and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

The invention claimed is:

1. An implant for augmentation, stabilisation, or defect reconstruction of bone tissue, comprising:
    a malleable scaffold portion having a same composition throughout and structured to provide shape to the implant, the malleable scaffold portion comprising:
    one or more polymers selected from polylactic acid isomer and/or polyglycolic acid polymer; and allogenic bone material, and
    an autologous cancellous bone graft and bone morphogenic protein embedded within the malleable scaffold portion,
    wherein the scaffold portion is in the form of a mesh or a lattice structure of customizable density.

2. The implant of claim 1, wherein the allogenic bone material comprises demineralized bone matrix.

3. A method for augmentation, stabilisation, or defect reconstruction of bone tissue, comprising: providing an implant, wherein the implant comprises:
    a malleable scaffold portion having a same composition throughout and structured to provide shape to the implant, wherein the malleable scaffold portion is in the form of a mesh or lattice structure of customizable density, the malleable scaffold portion comprising:
    one or more polymers selected from polylactic acid isomer and/or polyglycolic acid polymer;
    and allogenic bone material;
    embedding an autologous cancellous bone graft within the malleable scaffold portion;
    customizing the density of the mesh or lattice structure by tightening or loosening the mesh or lattice network; and
    applying the implant to a site of bone tissue in need of augmentation, stabilisation, or defect reconstruction.

4. The method of claim 3, wherein the allogenic bone material comprises demineralized bone matrix.

5. The method of claim 3, further comprising embedding bone morphogenic protein within the scaffold portion.

6. The method of claim 3 further comprising warming the malleable scaffold portion at the site in need of augmentation, stabilization, or defect reconstruction and intraoperatively modifying the warmed malleable scaffold portion.

* * * * *

UNITED STATES PATENT AND TRADEMARK OFFICE
CERTIFICATE OF CORRECTION

| | |
|---|---|
| PATENT NO. | : 10,987,448 B2 |
| APPLICATION NO. | : 15/843946 |
| DATED | : April 27, 2021 |
| INVENTOR(S) | : Jessica A. Ching et al. |

Page 1 of 1

It is certified that error appears in the above-identified patent and that said Letters Patent is hereby corrected as shown below:

In the Specification

Column 1, Line 30, "(PLEA" should be --(PLGA--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*